United States Patent
Sartor et al.

(10) Patent No.: US 11,241,272 B2
(45) Date of Patent: *Feb. 8, 2022

(54) BIPOLAR ELECTROSURGICAL INSTRUMENT WITH MOVABLE ELECTRODE AND RELATED SYSTEMS AND METHODS

(71) Applicant: Covidien LP, Mansfield, MA (US)

(72) Inventors: Joe D. Sartor, Longmont, CO (US); David N. Heard, Boulder, CO (US); Arlen K. Ward, Centennial, CO (US)

(73) Assignee: COVIDIEN LP, Mansfield, MA (US)

( * ) Notice: Subject to any disclaimer, the term of this patent is extended or adjusted under 35 U.S.C. 154(b) by 10 days.

This patent is subject to a terminal disclaimer.

(21) Appl. No.: 16/837,418

(22) Filed: Apr. 1, 2020

(65) Prior Publication Data
US 2020/0246059 A1 Aug. 6, 2020

Related U.S. Application Data

(63) Continuation of application No. 14/335,233, filed on Jul. 18, 2014, now Pat. No. 10,631,914.
(Continued)

(51) Int. Cl.
*A61B 18/14* (2006.01)
*A61B 18/00* (2006.01)

(52) U.S. Cl.
CPC ...... *A61B 18/14* (2013.01); *A61B 2018/0016* (2013.01); *A61B 2018/00023* (2013.01);
(Continued)

(58) Field of Classification Search
CPC ............ A61B 18/1442; A61B 18/1445; A61B 2018/1455; A61B 2017/2927; A61B 2017/2944
See application file for complete search history.

(56) References Cited

U.S. PATENT DOCUMENTS

| 2,888,928 A | 6/1959 | Seiger |
| D223,367 S | 4/1972 | Kountz |

(Continued)

FOREIGN PATENT DOCUMENTS

| CN | 1103807 C | 3/2003 |
| DE | 390937 C | 3/1924 |

(Continued)

OTHER PUBLICATIONS

U.S. Appl. No. 14/242,019, filed Apr. 1, 2014; inventor: Brannan.
(Continued)

*Primary Examiner* — Michael F Peffley
*Assistant Examiner* — Bo Ouyang
(74) *Attorney, Agent, or Firm* — Carter, DeLuca & Farrell LLP

(57) ABSTRACT

An electrosurgical device is provided that includes a handset having a shaft extending therefrom, a pair of active electrodes at a distal end of the shaft, and a movable, electrically floating electrode selectively positionable between the active electrodes. The floating electrode, when positioned to contact tissue between the active electrodes, modifies the electrosurgical current flows through tissue. The resultant modified current flows enables a surgeon to more effectively to control tissue desiccation by focusing electrosurgical energy toward targeted tissue and by reducing peripheral current flows. Embodiments are provided wherein the active electrodes include cooling provisions. Related electrosurgical systems and method of use are also provided.

19 Claims, 9 Drawing Sheets

Related U.S. Application Data

(60) Provisional application No. 61/884,573, filed on Sep. 30, 2013.

(52) U.S. Cl.
CPC ............ *A61B 2018/00589* (2013.01); *A61B 2018/1467* (2013.01); *A61B 2018/1475* (2013.01)

(56) References Cited

U.S. PATENT DOCUMENTS

| | | | |
|---|---|---|---|
| 3,682,130 A | 8/1972 | Jeffers | |
| 3,750,650 A | 8/1973 | Ruttgers | |
| 3,907,339 A | 9/1975 | Stumpf et al. | |
| 3,910,277 A | 10/1975 | Zimmer | |
| 3,924,628 A | 12/1975 | Droegemueller et al. | |
| 4,018,227 A | 4/1977 | Wallach | |
| 4,022,215 A | 5/1977 | Benson | |
| 4,060,088 A | 11/1977 | Morrison, Jr. et al. | |
| 4,061,135 A | 12/1977 | Widran et al. | |
| 4,063,560 A | 12/1977 | Thomas et al. | |
| 4,072,152 A | 2/1978 | Linehan | |
| 4,082,096 A | 4/1978 | Benson | |
| 4,207,897 A | 6/1980 | Lloyd et al. | |
| 4,244,371 A | 1/1981 | Farin | |
| 4,248,224 A | 2/1981 | Jones | |
| 4,275,734 A | 6/1981 | Mitchiner | |
| 4,276,874 A | 7/1981 | Wolvek et al. | |
| 4,278,090 A | 7/1981 | van Gerven | |
| D263,020 S | 2/1982 | Rau, III | |
| 4,321,931 A | 3/1982 | Hon | |
| 4,342,218 A | 8/1982 | Fox | |
| 4,355,642 A | 10/1982 | Alferness | |
| D266,842 S | 11/1982 | Villers et al. | |
| 4,381,007 A | 4/1983 | Doss | |
| D278,306 S | 4/1985 | McIntosh | |
| 4,519,389 A | 5/1985 | Gudkin et al. | |
| 4,598,698 A | 7/1986 | Siegmund | |
| 4,601,290 A | 7/1986 | Effron et al. | |
| 4,664,110 A | 5/1987 | Schanzlin | |
| 4,671,274 A | 6/1987 | Sorochenko | |
| 4,736,749 A | 4/1988 | Lundback | |
| D295,893 S | 5/1988 | Sharkany et al. | |
| D295,894 S | 5/1988 | Sharkany et al. | |
| 4,779,611 A | 10/1988 | Grooters et al. | |
| 4,802,475 A | 2/1989 | Weshahy | |
| 4,919,129 A | 4/1990 | Weber, Jr. et al. | |
| 4,931,047 A | 6/1990 | Broadwin et al. | |
| 5,197,964 A | 3/1993 | Parins | |
| 5,318,525 A | 6/1994 | West et al. | |
| 5,324,255 A | 6/1994 | Passafaro et al. | |
| 5,324,284 A | 6/1994 | Imran | |
| D354,218 S | 1/1995 | Van de Peer | |
| 5,396,887 A | 3/1995 | Imran | |
| 5,397,304 A | 3/1995 | Truckai | |
| 5,400,783 A | 3/1995 | Pomeranz et al. | |
| 5,427,119 A | 6/1995 | Swartz et al. | |
| 5,443,463 A | 8/1995 | Stern et al. | |
| 5,443,470 A | 8/1995 | Stern et al. | |
| 5,450,843 A | 9/1995 | Moll et al. | |
| 5,452,582 A | 9/1995 | Longsworth | |
| 5,452,733 A | 9/1995 | Sterman et al. | |
| 5,462,545 A | 10/1995 | Wang et al. | |
| 5,465,717 A | 11/1995 | Imran et al. | |
| 5,469,853 A | 11/1995 | Law et al. | |
| 5,478,309 A | 12/1995 | Sweezer et al. | |
| 5,478,330 A | 12/1995 | Imran et al. | |
| 5,486,193 A | 1/1996 | Bourne et al. | |
| 5,487,385 A | 1/1996 | Avitall | |
| 5,487,757 A | 1/1996 | Truckai et al. | |
| 5,496,312 A | 3/1996 | Klicek | |
| 5,497,774 A | 3/1996 | Swartz et al. | |
| 5,498,248 A | 3/1996 | Milder | |
| 5,500,012 A | 3/1996 | Brucker et al. | |
| 5,505,730 A | 4/1996 | Edwards | |
| 5,516,505 A | 5/1996 | McDow | |
| 5,520,682 A | 5/1996 | Baust et al. | |
| 5,522,870 A | 6/1996 | Ben-Zion | |
| 5,545,195 A | 8/1996 | Lennox et al. | |
| 5,549,661 A | 8/1996 | Kordis et al. | |
| 5,555,883 A | 9/1996 | Avitall | |
| 5,558,671 A | 9/1996 | Yates | |
| 5,560,362 A | 10/1996 | Sliwa, Jr. et al. | |
| 5,569,241 A | 10/1996 | Edwards | |
| 5,571,088 A | 11/1996 | Lennox et al. | |
| 5,571,215 A | 11/1996 | Sterman et al. | |
| 5,573,532 A | 11/1996 | Chang et al. | |
| 5,702,390 A * | 12/1997 | Austin | A61B 18/1445 606/48 |
| 5,906,615 A | 5/1999 | Thompson | |
| 5,971,983 A | 10/1999 | Lesh | |
| 5,993,447 A | 11/1999 | Blewett et al. | |
| 6,007,499 A | 12/1999 | Martin et al. | |
| 6,012,457 A | 1/2000 | Lesh | |
| 6,016,811 A | 1/2000 | Knopp et al. | |
| 6,042,556 A | 3/2000 | Beach et al. | |
| D424,693 S | 5/2000 | Pruter | |
| D424,694 S | 5/2000 | Tetzlaff et al. | |
| D425,201 S | 5/2000 | Tetzlaff et al. | |
| 6,056,744 A | 5/2000 | Edwards | |
| 6,056,745 A | 5/2000 | Panescu et al. | |
| 6,056,746 A | 5/2000 | Goble et al. | |
| 6,056,767 A | 5/2000 | Saadat et al. | |
| 6,063,081 A | 5/2000 | Mulier et al. | |
| 6,066,139 A | 5/2000 | Ryan et al. | |
| 6,068,653 A | 5/2000 | LaFontaine | |
| 6,071,279 A | 6/2000 | Whayne et al. | |
| 6,083,237 A | 7/2000 | Huitema et al. | |
| 6,086,585 A | 7/2000 | Hovda et al. | |
| 6,088,894 A | 7/2000 | Oakley | |
| 6,096,037 A | 8/2000 | Mulier et al. | |
| 6,113,592 A | 9/2000 | Taylor | |
| 6,113,596 A | 9/2000 | Hooven et al. | |
| 6,117,101 A | 9/2000 | Diederich et al. | |
| 6,120,496 A | 9/2000 | Whayne et al. | |
| 6,141,576 A | 10/2000 | Littmann et al. | |
| 6,142,993 A | 11/2000 | Whayne et al. | |
| 6,149,620 A | 11/2000 | Baker et al. | |
| 6,152,920 A | 11/2000 | Thompson et al. | |
| 6,161,543 A | 12/2000 | Cox et al. | |
| 6,165,174 A | 12/2000 | Jacobs et al. | |
| 6,190,384 B1 | 2/2001 | Ouchi | |
| 6,212,426 B1 | 4/2001 | Swanson | |
| 6,217,528 B1 | 4/2001 | Koblish et al. | |
| 6,217,575 B1 | 4/2001 | DeVore | |
| 6,217,576 B1 | 4/2001 | Tu et al. | |
| 6,224,592 B1 | 5/2001 | Eggers et al. | |
| 6,231,591 B1 | 5/2001 | Desai | |
| 6,235,020 B1 | 5/2001 | Cheng et al. | |
| 6,237,605 B1 | 5/2001 | Vaska et al. | |
| 6,238,347 B1 | 5/2001 | Nix et al. | |
| 6,238,387 B1 | 5/2001 | Miller, III | |
| 6,238,393 B1 | 5/2001 | Mulier | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,245,066 B1 | 6/2001 | Morgan et al. | |
| 6,251,092 B1 | 6/2001 | Qin et al. | |
| 6,251,110 B1 | 6/2001 | Wampler | |
| 6,251,128 B1 | 6/2001 | Knopp et al. | |
| 6,258,087 B1 | 7/2001 | Edwards et al. | |
| 6,264,650 B1 | 7/2001 | Hovda et al. | |
| 6,266,551 B1 | 7/2001 | Osadchy et al. | |
| 6,270,471 B1 | 8/2001 | Hechel et al. | |
| 6,283,988 B1 | 9/2001 | Laufer et al. | |
| 6,283,989 B1 | 9/2001 | Laufer et al. | |
| 6,293,943 B1 | 9/2001 | Panescu et al. | |
| D449,886 S | 10/2001 | Tetzlaff et al. | |
| 6,299,633 B1 | 10/2001 | Laufer | |
| 6,302,880 B1 | 10/2001 | Schaer | |
| 6,311,692 B1 | 11/2001 | Vaska et al. | |
| 6,312,383 B1 | 11/2001 | Lizzi et al. | |
| 6,314,962 B1 | 11/2001 | Vaska et al. | |

(56) References Cited

U.S. PATENT DOCUMENTS

| | | | |
|---|---|---|---|
| 6,322,559 B1 | 11/2001 | Daulton et al. |
| 6,328,736 B1 | 12/2001 | Mulier |
| 6,332,881 B1 | 12/2001 | Carner et al. |
| 6,358,248 B1 | 3/2002 | Mulier et al. |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| D457,958 S | 5/2002 | Dycus et al. |
| D457,959 S | 5/2002 | Tetzlaff et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey et al. |
| 6,413,254 B1 | 7/2002 | Hissong et al. |
| 6,416,509 B1 | 7/2002 | Goble et al. |
| 6,419,648 B1 | 7/2002 | Vitek et al. |
| 6,430,426 B2 | 8/2002 | Avitall |
| 6,440,130 B1 | 8/2002 | Mulier et al. |
| 6,443,952 B1 | 9/2002 | Mulier et al. |
| 6,451,016 B1 | 9/2002 | Karakozian |
| 6,461,314 B1 | 10/2002 | Pant et al. |
| 6,461,956 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier et al. |
| 6,477,396 B1 | 11/2002 | Mest et al. |
| 6,484,727 B1 | 11/2002 | Vaska et al. |
| 6,488,680 B1 | 12/2002 | Francischelli et al. |
| 6,502,575 B1 | 1/2003 | Jacobs et al. |
| 6,508,815 B1 | 1/2003 | Strul et al. |
| 6,514,250 B1 | 2/2003 | Jahns et al. |
| 6,517,536 B2 | 2/2003 | Hooven et al. |
| 6,527,767 B2 | 3/2003 | Wang et al. |
| 6,537,248 B2 | 3/2003 | Muller |
| 6,537,272 B2 | 3/2003 | Christopherson et al. |
| 6,558,379 B1 | 5/2003 | Batchelor et al. |
| 6,558,382 B2 | 5/2003 | Jahns |
| 6,558,385 B1 | 5/2003 | McClurken et al. |
| 6,575,969 B1 | 6/2003 | Rittman, III et al. |
| 6,584,360 B2 | 6/2003 | Francischelli |
| 6,585,732 B2 | 7/2003 | Muller |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier et al. |
| 6,613,048 B2 | 9/2003 | Mulier et al. |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli et al. |
| 6,656,175 B2 | 12/2003 | Francischelli et al. |
| 6,663,627 B2 | 12/2003 | Francischelli et al. |
| 6,666,862 B2 | 12/2003 | Jain et al. |
| 6,679,882 B1 | 1/2004 | Kornerup |
| 6,682,501 B1 | 1/2004 | Nelson |
| D487,039 S | 2/2004 | Webster et al. |
| 6,689,131 B2 | 2/2004 | McClurken |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli et al. |
| 6,706,039 B2 | 3/2004 | Muller |
| 6,716,211 B2 | 4/2004 | Muller |
| 6,730,075 B2 | 5/2004 | Palanker et al. |
| 6,736,810 B2 | 5/2004 | Hoey et al. |
| 6,755,827 B2 | 6/2004 | Muller |
| 6,764,487 B2 | 7/2004 | Mulier et al. |
| 6,766,202 B2 | 7/2004 | Underwood et al. |
| 6,766,817 B2 | 7/2004 | da Silva |
| 6,773,433 B2 | 8/2004 | Stewart et al. |
| 6,776,780 B2 | 8/2004 | Mulier et al. |
| 6,780,178 B2 | 8/2004 | Palanker et al. |
| D496,997 S | 10/2004 | Dycus et al. |
| 6,807,968 B2 | 10/2004 | Francischelli |
| D499,181 S | 11/2004 | Dycus et al. |
| 6,827,713 B2 | 12/2004 | Bek et al. |
| 6,827,715 B2 | 12/2004 | Francischelli et al. |
| 6,832,996 B2 | 12/2004 | Woloszko et al. |
| 6,849,073 B2 | 2/2005 | Hoey et al. |
| 6,858,028 B2 | 2/2005 | Mulier et al. |
| 6,881,213 B2 | 4/2005 | Ryan et al. |
| 6,887,238 B2 | 5/2005 | Jahns |
| 6,899,711 B2 | 5/2005 | Stewart et al. |
| 6,911,019 B2 | 6/2005 | Muller |
| 6,913,605 B2 | 7/2005 | Fletcher et al. |
| 6,915,806 B2 | 7/2005 | Pacek et al. |
| 6,916,318 B2 | 7/2005 | Francischelli et al. |
| 6,942,661 B2 | 9/2005 | Swanson |
| 6,949,097 B2 | 9/2005 | Stewart et al. |
| 6,949,098 B2 | 9/2005 | Muller |
| 6,953,461 B2 | 10/2005 | McClurken et al. |
| 6,960,205 B2 | 11/2005 | Jahns |
| 6,962,589 B2 | 11/2005 | Muller |
| 7,066,586 B2 | 6/2006 | da Silva |
| D525,361 S | 7/2006 | Hushka |
| D531,311 S | 10/2006 | Guerra et al. |
| 7,115,139 B2 | 10/2006 | McClurken et al. |
| D533,942 S | 12/2006 | Kerr et al. |
| D535,027 S | 1/2007 | James et al. |
| 7,156,845 B2 | 1/2007 | Mulier et al. |
| 7,166,106 B2 | 1/2007 | Bartel et al. |
| 7,189,233 B2 | 3/2007 | Truckai et al. |
| D541,418 S | 4/2007 | Schechter et al. |
| D541,938 S | 5/2007 | Kerr et al. |
| 7,232,440 B2 | 6/2007 | Dumbauld et al. |
| 7,238,185 B2 | 7/2007 | Palanker et al. |
| 7,247,155 B2 | 7/2007 | Hoey et al. |
| 7,309,325 B2 | 12/2007 | Mulier et al. |
| 7,311,708 B2 | 12/2007 | McClurken |
| 7,322,974 B2 | 1/2008 | Swoyer et al. |
| D564,662 S | 3/2008 | Moses et al. |
| 7,357,802 B2 | 4/2008 | Palanker et al. |
| 7,364,579 B2 | 4/2008 | Mulier et al. |
| 7,367,974 B2 | 5/2008 | Haemmerich et al. |
| D576,932 S | 9/2008 | Strehler |
| 7,419,488 B2 * | 9/2008 | Ciarrocca .......... A61B 18/1402 606/41 |
| 7,445,617 B2 | 11/2008 | Eastwood et al. |
| 7,537,595 B2 | 5/2009 | McClurken |
| D594,736 S | 6/2009 | Esjunin |
| D594,737 S | 6/2009 | Kelly et al. |
| 7,604,635 B2 | 10/2009 | McClurken et al. |
| D606,203 S | 12/2009 | Husheer et al. |
| 7,645,277 B2 | 1/2010 | McClurken et al. |
| 7,651,494 B2 | 1/2010 | McClurken et al. |
| D613,412 S | 4/2010 | DeCarlo |
| 7,727,232 B1 | 6/2010 | Maurer et al. |
| 7,736,361 B2 | 6/2010 | Palanker et al. |
| 7,789,879 B2 | 9/2010 | Palanker et al. |
| 7,811,282 B2 | 10/2010 | McClurken |
| 7,815,634 B2 | 10/2010 | McClurken et al. |
| D634,010 S | 3/2011 | DeCarlo |
| 7,909,820 B2 | 3/2011 | Lipson et al. |
| 7,951,148 B2 | 5/2011 | McClurken |
| 7,972,330 B2 | 7/2011 | Alejandro et al. |
| 7,976,544 B2 | 7/2011 | McClurken et al. |
| 7,998,140 B2 | 8/2011 | McClurken et al. |
| 8,038,670 B2 | 10/2011 | McClurken |
| 8,043,286 B2 | 10/2011 | Palanker et al. |
| 8,048,070 B2 | 11/2011 | O'Brien et al. |
| 8,075,557 B2 | 12/2011 | Maurer et al. |
| 8,083,736 B2 | 12/2011 | McClurken et al. |
| 8,105,324 B2 | 1/2012 | Palanker et al. |
| 8,137,345 B2 | 3/2012 | McNall, III et al. |
| 8,177,783 B2 | 5/2012 | Davison et al. |
| 8,216,233 B2 | 7/2012 | McClurken et al. |
| 8,235,989 B2 | 8/2012 | Palanker et al. |
| 8,323,276 B2 | 12/2012 | Palanker et al. |
| 8,348,946 B2 | 1/2013 | McClurken et al. |

(56) References Cited

U.S. PATENT DOCUMENTS

| | | |
|---|---|---|
| 8,361,068 B2 | 1/2013 | McClurken |
| 8,414,572 B2 | 4/2013 | Davison et al. |
| D681,810 S | 5/2013 | DeCarlo |
| 8,475,455 B2 | 7/2013 | McClurken et al. |
| 8,506,564 B2 | 8/2013 | Long et al. |
| 8,568,409 B2 | 10/2013 | O'Brien et al. |
| 8,632,533 B2 | 1/2014 | Greeley et al. |
| 8,870,864 B2 | 10/2014 | Davison et al. |
| 8,882,756 B2 | 11/2014 | Greeley et al. |
| 8,906,012 B2 | 12/2014 | Conley et al. |
| 8,920,417 B2 | 12/2014 | Conley et al. |
| 8,979,842 B2 | 3/2015 | McNall, III et al. |
| 9,011,445 B2 | 4/2015 | Greeley |
| 9,018,983 B2 | 4/2015 | Vankov |
| 9,023,040 B2 | 5/2015 | Bloom et al. |
| 9,050,113 B2 | 6/2015 | Bloom et al. |
| 9,131,980 B2 | 9/2015 | Bloom |
| 9,138,289 B2 | 9/2015 | Conley et al. |
| 9,226,792 B2 | 1/2016 | Bloom |
| 9,254,168 B2 | 2/2016 | Palanker |
| 9,333,027 B2 | 5/2016 | Bloom et al. |
| 9,345,541 B2 | 5/2016 | Greeley et al. |
| 9,381,061 B2 | 7/2016 | McClurken et al. |
| 9,427,281 B2 | 8/2016 | Bloom et al. |
| 9,445,858 B2 | 9/2016 | Conley et al. |
| 9,486,283 B2 | 11/2016 | Greeley et al. |
| 10,631,914 B2 | 4/2020 | Sartor et al. |
| 2001/0051802 A1 | 12/2001 | Woloszko et al. |
| 2002/0111624 A1 | 8/2002 | Witt et al. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0078578 A1 | 4/2003 | Truckai et al. |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0019350 A1 | 1/2004 | O'Brien et al. |
| 2004/0024395 A1 | 2/2004 | Ellman et al. |
| 2004/0044340 A1 | 3/2004 | Francischelli |
| 2004/0049179 A1 | 3/2004 | Francischelli et al. |
| 2004/0078069 A1 | 4/2004 | Francischelli |
| 2004/0082948 A1 | 4/2004 | Stewart et al. |
| 2004/0087940 A1 | 5/2004 | Jahns et al. |
| 2004/0092926 A1 | 5/2004 | Hoey |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey et al. |
| 2004/0220560 A1 | 11/2004 | Briscoe |
| 2004/0236322 A1 | 11/2004 | Muller |
| 2004/0267326 A1 | 12/2004 | Ocel et al. |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0124987 A1* | 6/2005 | Goble ............... A61B 18/1442 606/50 |
| 2005/0143729 A1 | 6/2005 | Francischelli |
| 2005/0165392 A1 | 7/2005 | Francischelli |
| 2005/0209564 A1 | 9/2005 | Bonner et al. |
| 2005/0267454 A1 | 12/2005 | Hissong |
| 2005/0267467 A1 | 12/2005 | Paul et al. |
| 2006/0009756 A1 | 1/2006 | Francischelli et al. |
| 2006/0009759 A1 | 1/2006 | Chrisitian et al. |
| 2006/0064085 A1 | 3/2006 | Schechter et al. |
| 2006/0217709 A1 | 9/2006 | Couture et al. |
| 2007/0049920 A1 | 3/2007 | McClurken et al. |
| 2007/0093808 A1 | 4/2007 | Mulier et al. |
| 2007/0112343 A1 | 5/2007 | Mische et al. |
| 2007/0118114 A1 | 5/2007 | Miller et al. |
| 2007/0208332 A1 | 9/2007 | Mulier et al. |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0234674 A1 | 9/2008 | McClurken et al. |
| 2009/0209975 A1 | 8/2009 | Milijasevic et al. |
| 2009/0222001 A1 | 9/2009 | Greeley et al. |
| 2009/0264879 A1 | 10/2009 | McClurken et al. |
| 2010/0076433 A1 | 3/2010 | Taylor et al. |
| 2010/0100095 A1 | 4/2010 | McClurken et al. |
| 2011/0028965 A1 | 2/2011 | McClurken et al. |
| 2011/0290854 A1 | 12/2011 | Timm et al. |
| 2011/0306968 A1 | 12/2011 | Beckman |
| 2012/0004657 A1 | 1/2012 | Conley et al. |
| 2012/0010149 A1 | 1/2012 | McClurken et al. |
| 2012/0116397 A1 | 5/2012 | Rencher et al. |
| 2012/0191084 A1 | 7/2012 | Davison et al. |
| 2012/0199631 A1 | 8/2012 | Shelton, IV et al. |
| 2012/0323227 A1 | 12/2012 | Wolf |
| 2014/0188105 A1 | 7/2014 | Conley et al. |
| 2015/0320490 A1 | 11/2015 | Conley et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0246350 A1 | 11/1987 |
| EP | 0521264 A2 | 1/1993 |
| EP | 0556705 A1 | 8/1993 |
| EP | 0558429 A1 | 9/1993 |
| EP | 0648515 A1 | 4/1995 |
| EP | 0836868 A2 | 4/1998 |
| EP | 0882955 A1 | 12/1998 |
| EP | 1159926 A2 | 3/2003 |
| FR | 179 607 | 11/1906 |

(56) References Cited

FOREIGN PATENT DOCUMENTS

| | | |
|---|---|---|
| FR | 1275415 A | 11/1961 |
| FR | 1347865 A | 1/1964 |
| FR | 2 235 669 A1 | 1/1975 |
| FR | 2 276 027 A1 | 1/1976 |
| FR | 2313708 A1 | 12/1976 |
| FR | 2502935 A1 | 10/1982 |
| FR | 2517953 A1 | 6/1983 |
| FR | 2573301 A1 | 5/1986 |
| FR | 2 862 813 A1 | 5/2005 |
| FR | 2 864 439 A1 | 7/2005 |
| JP | 56161636 | 12/1981 |
| JP | 5958933 | 4/1984 |
| JP | 55106 | 1/1993 |
| JP | 508933 | 2/1993 |
| JP | 0540112 | 2/1993 |
| JP | 06343644 | 12/1994 |
| JP | 07265328 | 10/1995 |
| JP | 08056955 | 3/1996 |
| JP | 08252263 A | 10/1996 |
| JP | 09000492 A | 1/1997 |
| JP | 09010223 | 1/1997 |
| JP | 9117456 | 5/1997 |
| JP | 11244298 | 9/1999 |
| JP | 2000342599 A | 12/2000 |
| JP | 2000350732 A | 12/2000 |
| JP | 2001003776 A | 1/2001 |
| JP | 2001008944 | 1/2001 |
| JP | 2001029356 | 2/2001 |
| JP | 2001037775 | 2/2001 |
| JP | 2001128990 A | 5/2001 |
| JP | 2001231870 A | 8/2001 |
| JP | 2002253569 A | 9/2002 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 11/1964 |
| SU | 401367 A1 | 10/1973 |
| SU | 727201 A2 | 4/1980 |
| WO | 0036985 A2 | 6/2000 |
| WO | 2010035831 A1 | 4/2010 |

OTHER PUBLICATIONS

U.S. Appl. No. 14/242,048, filed Apr. 1, 2014; inventor: Prakash.
U.S. Appl. No. 14/281,264, filed May 19, 2014; inventor: Prakash.
U.S. Appl. No. 14/281,344, filed May 19, 2014; inventor: Shiu.
U.S. Appl. No. 14/300,824, filed Jun. 10, 2014; inventor: Behnke.
U.S. Appl. No. 14/300,871, filed Jun. 10, 2014; inventor: Bonn.
U.S. Appl. No. 14/306,865, filed Jun. 17, 2014; inventor: Brannan.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok. TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division. (Products Price List), one page, Jul. 19, 2000.
Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology vol. 102, No. 1, Jul. 2003.
B. Levy M.D. et al., "Update on Hysterectomy New Technologies and Techniques" OBG Management. Feb. 2003.
B. Levy M.D.. "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1, (Jul. 1991) pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
D. H. Durney et al.. "Antennas for Medical Applications", Antenna Handbook: Theory Application and Design, p. 24-40. Van Nostrand Reinhold, 1988 New York, V.T. Lo, S.W. Lee.
Carbonell et al., "Comparison of the Gyrus PlasmaKinetic Sealer and the Valleylab LigaSure. TM. Device in the Hemostasis of Small, Medium, and Large-Sized Arteries" Carolinas Laparoscopic and Advanced Surgery Program, Carolinas MedicalCenter,Charlotte, NC 2003.
Carus et al., "Initial Experience With the LigaSure. TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V Amsterdam, NL, vol. 52. No. 3.
Chou, C.K., (1995) "Radiofrequency Hyperthermia in Cancer Therapy," Chapter 941n Biologic Effects of Nonionizing Electromagnetic Fields, CRC Press, Inc, pp. 1424-1428.
Chung et al., "Clinical Experience of Sutureless Closed Hemorrhoidectomy with LigaSureTM " Diseases of the Colon & Rectum, vol. 46, No. 1, Jan. 2003.
Cosman et al., "Methods of Making Nervous System Lesions", In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone", Neurosurgery 15:(1984) pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al. "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts". Nov. 1, 2003; 4 pages.
Geddes et al.. "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vase. Interv. Radiol, vol. 12, pp. 1021-1032.
Goldberg et al. (1995) "Saline-enhanced RF Ablation: Demonstration of Efficacy and Optimization of Parameters", Radiology, 197(P): 140(Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.

(56) References Cited

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite Element Codes To Model Electrical Heating And Non-Linear Thermal Transport In Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1. pp. 307-320.
Jarrett et al., "Use of the LigaSureTM Vessel Sealing System for Peri-Hilar Vessels in Laparoscopic Nephrectomy" Sales/Product Literature 2000.
Johnson et al. "Evaluation of a Bipolar Electrothermal Vessel Sealing Device in Hemorrhoidectomy" Sales/Product Literature; Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole, M.D., et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al. "High-burst-strength, feedback-controlled bipolar vessel sealing" Surgical Endoscopy (1998) 12:876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSureTM Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May-Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page; Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform": Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002, 89, 154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001 pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons 190(6):692-699.
Valleylab Brochure. "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'L Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Stagegaard, N., Petersen H.H., Chen X., Svendsen J.H., "Indication of the Radiofrequency Induced Lesion Size by Pre-ablation Measurements" Europace (2005) 7, 525-534.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.

(56) References Cited

OTHER PUBLICATIONS

T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: TargisTM Technology (Date Unknown). "Overcoming the Challenge" located at <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 14/011,414, filed Aug. 27, 2013; inventor: Ohri.
U.S. Appl. No. 14/011,438, filed Aug. 27, 2013; inventor: Ohri.

\* cited by examiner

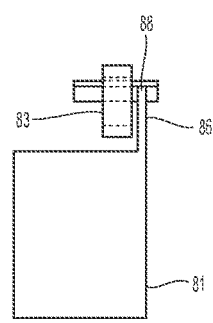
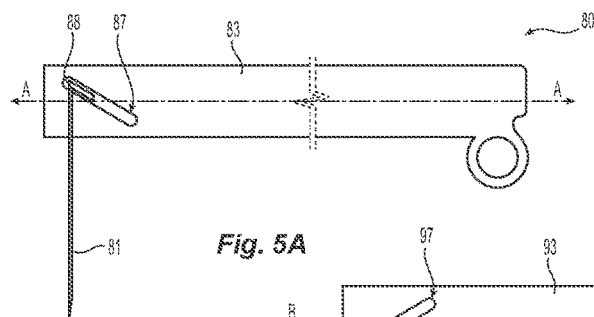
Fig. 5C
Fig. 5A
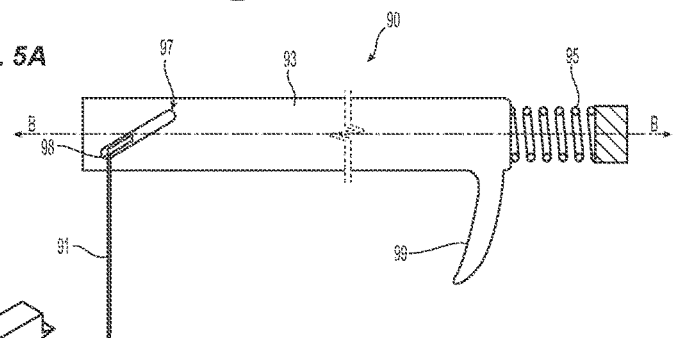
Fig. 6A
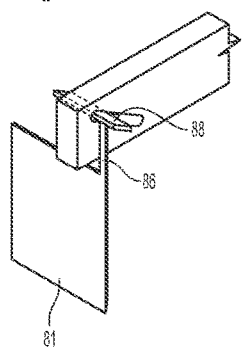
Fig. 5B
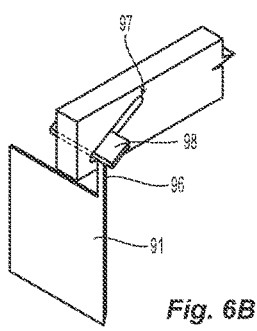
Fig. 6B

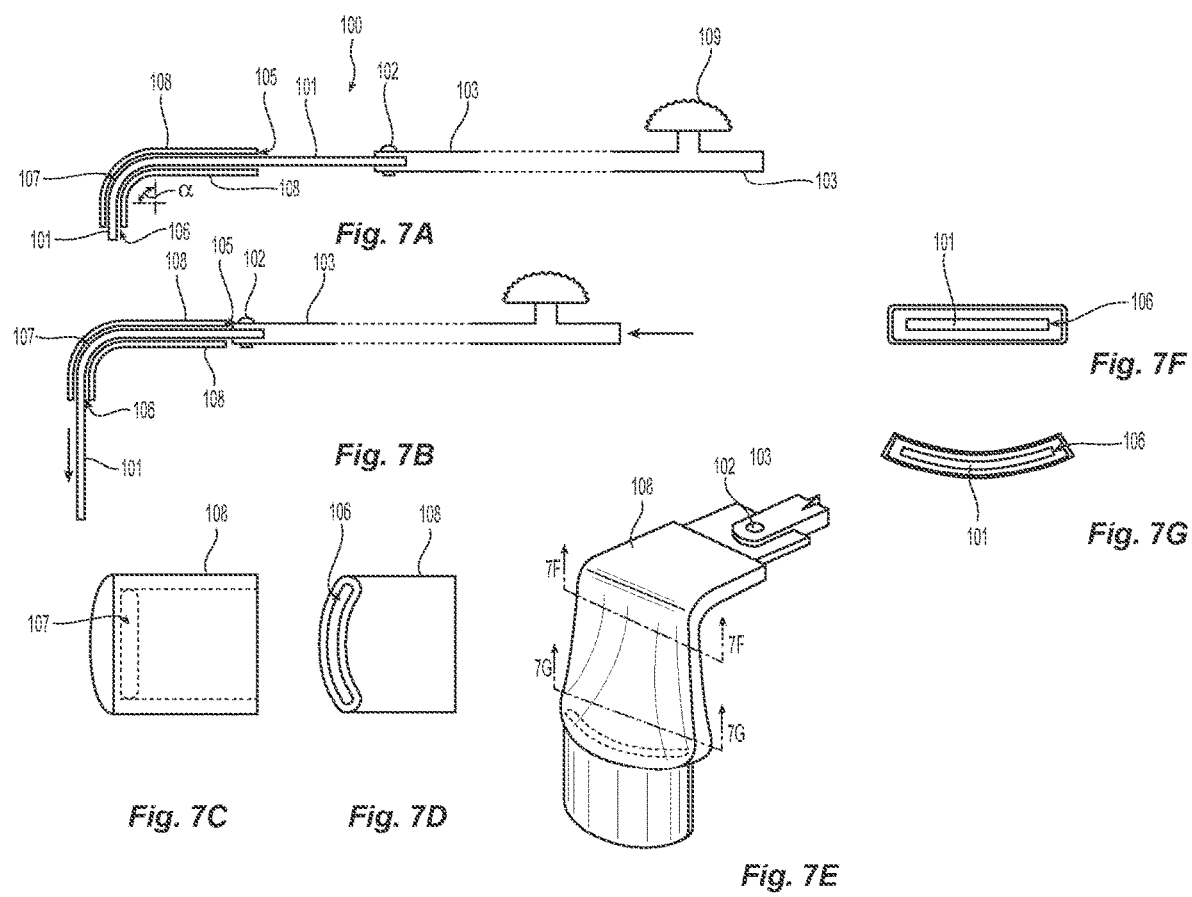

BIPOLAR ELECTROSURGICAL INSTRUMENT WITH MOVABLE ELECTRODE AND RELATED SYSTEMS AND METHODS

CROSS REFERENCE TO RELATED APPLICATIONS

This application is a continuation of U.S. patent application Ser. No. 14/335,233, filed on Jul. 18, 2014, which claims the benefit of and priority to U.S. Provisional Patent Application Ser. No. 61/884,573, filed on Sep. 30, 2013, the entire disclosures of each of which are incorporated by reference herein.

BACKGROUND

Technical Field

The present disclosure relates to a bipolar electrosurgical instrument configured to provide controlled deep tissue desiccation. More particularly, the present disclosure relates to an electrosurgical instrument that includes a pair of electrodes and a movable floating electrode that enables a surgeon to effectively control tissue desiccation.

Background of Related Art

Electrosurgical devices, such as surface tissue desiccation devices are well known in the medical arts and typically include a handset with an on/off switch, a shaft, and at least one electrode operatively coupled to a distal end of the shaft that is configured to perform an electrosurgical procedure, such as surface or deep tissue desiccation. Such electrosurgical devices utilize electrical energy to effectuate hemostasis and desiccation by heating the tissue and blood vessels. Such devices include electrocautery pencils, forceps, and probes of various types and configurations from a number of different manufacturers. The algorithms used with these electrosurgical devices in surgical treatments typically seek to provide a desired amount of delivered energy in accordance with the power level and duration specified by the surgeon.

Electrosurgical devices which utilize this electrical energy for performing deep tissue coagulation and desiccation during orthopedic procedures, such as spinal and joint replacement surgery, may have drawbacks which influence surgical outcomes. For example, a typical issue is the inability of a surgeon to reliably and selectively control tissue treatment depth during desiccation procedures. It has been observed that during desiccation procedures, surgeons tend to manipulate tissue with the electrodes of the device to retract and separate tissue. This technique, however, may extend operative times and/or cause unsatisfactory results due to varying contact area between the electrode and tissue as the instrument is manipulated.

SUMMARY

In view of the foregoing, an electrosurgical instrument that includes a pair of electrodes and a movable floating electrode that enables a surgeon to effectively control tissue desiccation, and associated systems and methods of use, would be a welcome advance in the state of the art.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

As it is used herein, "electrosurgical procedure" generally refers to any electrosurgical procedure involving any form of energy, such as, for example, microwave energy and radiofrequency (RF) energy.

In one aspect of the present disclosure, an electrosurgical instrument is provided. The electrosurgical instrument includes a handle having a shaft extending distally therefrom, a first active electrode and a second active electrode disposed in spaced relation on a distal end of the shaft, and a floating electrode or electrode selectively positionable between an extended position where the floating electrode is disposed within an area between the first active electrode and a second active electrode, and a retracted position where the floating electrode is removed from the area between the first active electrode and a second active electrode. The first active electrode and a second active electrode may be configured to couple to a source of electrosurgical energy. The first active electrode, the second active electrode, and the floating electrode may each include a tissue-contacting surface.

In some embodiments, when the floating electrode is in the extended position, the tissue-contacting surfaces of the first active electrode, the second active electrode, and the floating electrode lie substantially in the same plane. The active electrodes may be configured to operate in a bipolar mode of operation.

In other embodiments, the electrosurgical instrument includes a coolant supply conduit configured to deliver coolant to the first active electrode and the second active electrode, and a coolant return conduit configured to remove coolant from the first active electrode and the second active electrode. In yet other embodiments, the first and second active electrodes are each in thermal communication with a heat pipe that is configured to draw heat from the first and second active electrodes to the ambient atmosphere.

The electrosurgical instrument may include a drive mechanism having a drive member movable along a longitudinal axis of the shaft between a first position and a second position, a cam slot defined in a distal end of the drive member, and a follower fixed to the floating electrode and configured to operably engage the cam slot. When the drive member is in a first position the floating electrode is in the extended position, and wherein when the drive member is in a second position, the floating electrode is in the retracted position.

In an alternative embodiment, the drive mechanism may include a drive member movable along a longitudinal axis of the shaft between a first position and a second position and an electrode guide. The electrode guide may include an elongated entrance opening defined at an entrance end of the electrode guide having an entrance direction and an elongated exit opening defined at an exit end of the electrode guide and having an exit direction different from the entrance direction. The electrode guide may include a channel joining the entrance opening and the exit opening and include an elbow transitioning the channel from the entrance direction to the exit direction. The cross section of the channel at the elbow may have an elongated rectangular shape, and the cross section of the channel at the exit opening may have a curved elongated rectangular shape. The floating electrode may be formed from a strip of flexible material positioned, in part, within the electrode guide, and operably coupled to a distal end of the drive member.

In another aspect of the present disclosure, an electrosurgical system is provided. The disclosed electrosurgical system includes an electrosurgical generator and an electrosurgical instrument as described above. The electrosurgical generator and the pair of electrodes may be configured to operate in a bipolar mode of operation.

In yet another aspect of the present disclosure, a method for electrosurgically treating tissue is provided. The disclosed method includes the steps of providing an electrosurgical device as described above, applying the first active electrode and the second active electrode to tissue, and delivering electrosurgical energy to tissue via the first active electrode and the second active electrode. The method may include the steps of applying the floating electrode to tissue and/or removing the floating electrode from tissue.

BRIEF DESCRIPTION OF THE DRAWINGS

Various embodiments of the present disclosure are described hereinbelow with references to the drawings, wherein:

FIG. 5A is a detail, side view of a floating electrode and a drive member of an electrosurgical instrument in accordance with an embodiment of the present disclosure;

FIG. 5B is a detail, perspective view of a floating electrode and a drive member of the FIG. 5A embodiment;

FIG. 5C is an end view of a drive member of a floating electrode and a drive member of the FIG. 5A embodiment;

FIG. 6A is a detail, side view of a floating electrode and a drive member of an electrosurgical instrument in accordance with another embodiment of the present disclosure;

FIG. 6B is a detail, perspective view of a floating electrode and a drive member of the FIG. 6A embodiment;

FIG. 7A is a side view of a deployable floating electrode in a raised position in accordance with yet another embodiment of the present disclosure;

FIG. 7B is a side view of a deployable floating electrode in a lowered position in accordance with the FIG. 7A embodiment;

FIG. 7C is a top view of a floating electrode guide in accordance with the FIG. 7A embodiment;

FIG. 7D is a bottom view of a floating electrode guide in accordance with the FIG. 7A embodiment;

FIG. 7E is a perspective view of a floating electrode and guide in accordance with the FIG. 7A embodiment;

FIG. 7F is a section view of a floating electrode guide in accordance with the FIG. 7A embodiment; and FIG. 7G is another section view of the floating electrode guide in accordance with the FIG. 7A embodiment.

DETAILED DESCRIPTION

Figure 1:
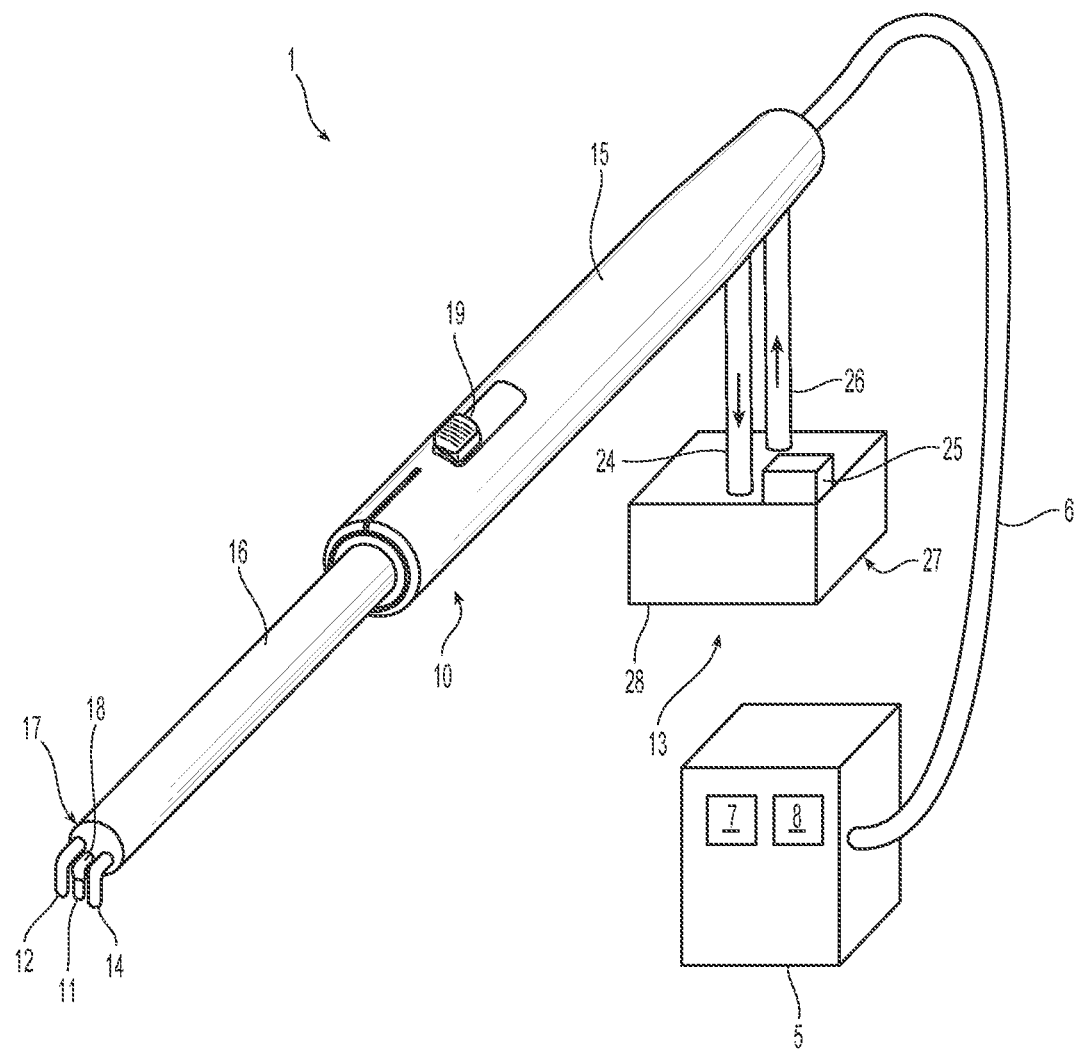
FIG. 1 is a perspective view of a system for electrosurgically treating tissue according to an embodiment of the present disclosure.

Particular embodiments of the present disclosure are described hereinbelow with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In this description, as well as in the drawings, like-referenced numbers represent elements which may perform the same, similar, or equivalent functions; the term "proximal," as is traditional, shall refer to the end of the instrument that is closer to the user, while the term "distal" shall refer to the end that is farther from the user. In addition, references to positive (+) and negative (−) are for illustrative purposes only, and it is to be understood that the polarity of the described elements may vary over time in accordance with the alternating current nature of electrosurgical energy.

Referring to FIG. 1, there is shown a perspective view of an electrosurgical system 1 including a generator 5 having a controller 7, and an electrosurgical instrument 10 for electrosurgically treating tissue according to an embodiment of the present disclosure. A coolant unit 27 is provided for delivering fluid to electrodes 12, 14 of electrosurgical instrument 10. Cooling unit 27 includes a coolant reservoir 28 in which a supply of coolant may be maintained, such as, without limitation, deionized water, glycol, saline, and the like. Cooling unit 27 may include a coolant pump 25 that is configured to circulate coolant between reservoir 28 and instrument 10 via coolant supply conduit 26 and coolant return conduit 24. Coolant supply conduit 26 and coolant return conduit 24 are electrically isolated from one other. In some embodiments, the cooling fluid circulated through coolant supply conduit 26 and coolant return conduit 24 is a non-conducting or a low conductive substance.

Continuing with reference to FIG. 1, generator 5 is configured to generate and deliver electrosurgical energy, e.g., radio frequency energy, to active electrodes 12 and 14, for performing electrosurgical procedures. The electrosurgical procedures may include cutting, cauterizing, coagulating, desiccating, and fulgurating tissue; all of which may employ RF energy. Generator 5 may be configured for monopolar and/or bipolar modes of operation. For illustrative purposes, generator 5 and, hence, system 1, is shown configured for a bipolar mode of operation.

Generator 5 includes one or more processors 8 that are in operative communication with controller 7 and configured to transmit electrosurgical energy, which may be in the form of a wave or signal/pulse, via cable 6 to instrument 10. Controller 7 and/or processor 8 may include one or more control algorithms that regulate the delivery of electrosurgical energy to tissue in accordance with an impedance of an electrode-tissue interface. One or more data lookup tables accessible by controller 7 and/or processor 8 may utilized to store relevant information relating to impedance and/or energy delivery. This information relating to impedance and/or pressure may be acquired empirically and/or calculated utilizing one or more suitable equations.

In the embodiment illustrated in FIG. 1, instrument 10 is shown as a bipolar electrocautery pencil (such as the one described in commonly-owned U.S. Pat. No. 7,621,909 to Buchman II, et al.) that includes a proximal handle 15 and a distal shaft 16. Handle 15 includes a slide actuator 19 that is configured to selectively position a movable, electrically floating electrode 11 between active electrode 12 and active electrode 14. Floating electrode 11 is formed from conductive material, and may be lowered (extended) and raised (retracted) between electrodes 12 and 14 to alter the energy field formed therebetween during electrosurgical procedures. In the embodiment illustrated in FIG. 1, moving slide actuator 19 distally causes floating electrode 11 to lower between electrodes 12 and 14. Conversely, moving slide actuator 19 proximally retracts floating electrode 11. In other embodiments, floating electrode 11 may be lowered by moving slide actuator 19 proximally and raised by moving slide actuator 19 distally. In yet other embodiments, a trigger actuator, a rotary actuator, or motorized actuator may be employed to extend and retract floating electrode 11.

Shaft 16 extends distally from handle 15, and active electrode 12 and active electrode 14 are disposed at a distal end 17 of shaft 16. In some embodiments, a guide 18 is operatively associated with floating electrode 11 to facilitate the selective positioning thereof.

In some embodiments, instrument 10 may be configured for a monopolar mode of operation. In these embodiments, one or both of the active electrodes 12 or 14 is configured to deliver monopolar electrosurgical energy to tissue, and a return pad (not explicitly shown) may be positioned on a patient and utilized as a return electrode.

Figure 2A:
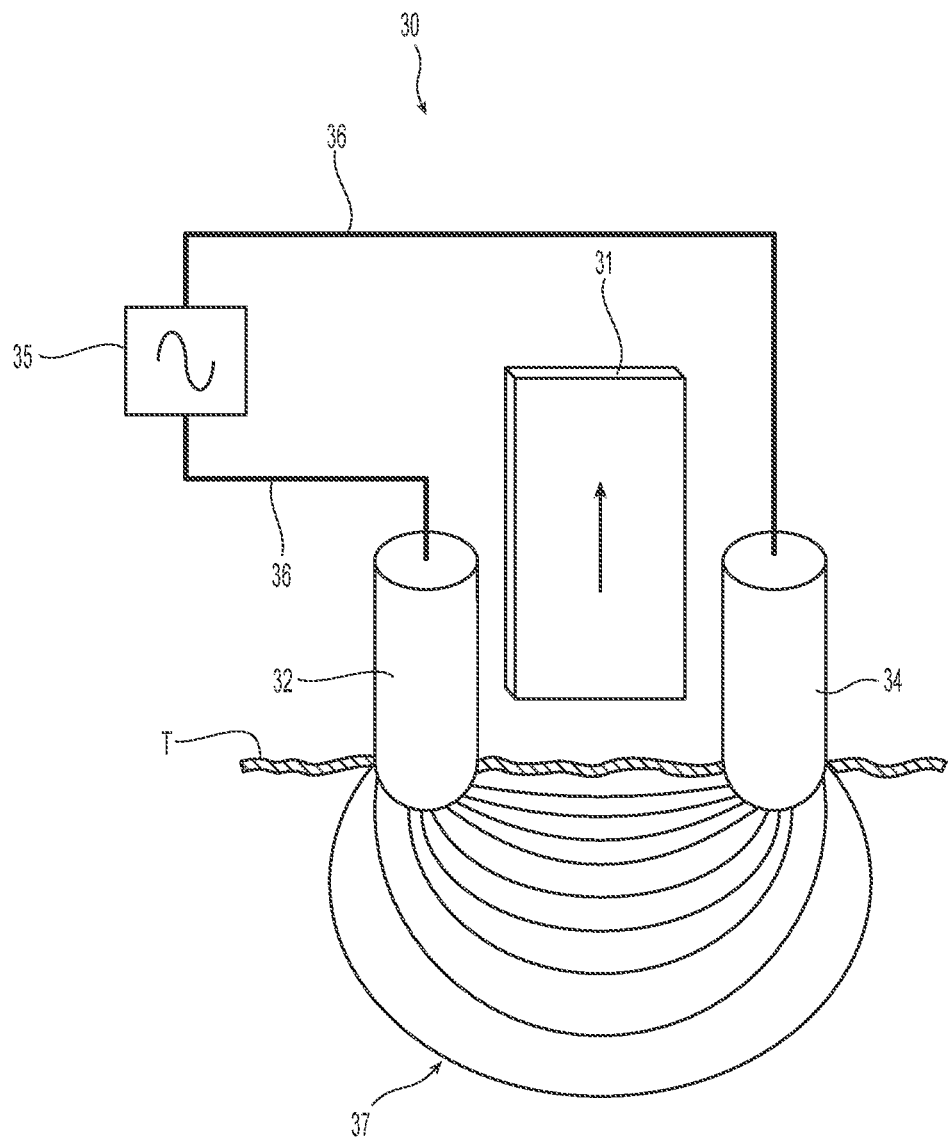
FIG. 2A is a schematic view of bipolar electrodes and a floating electrode in a raised configuration in accordance with an embodiment of the present disclosure.

Advantageously, use of the movable floating electrode 11 in accordance with the present disclosure enables a surgeon to selectively control the intensity and/or depth of the electrosurgical effect from the adjacent electrodes 12, 14. This advantage is illustrated in detail with reference to FIGS. 2A and 2B. As shown in FIG. 2A, an electrode assembly 30 includes a first electrode 32 and a second electrode 34 positioned in a fixed, spaced relation to one another and coupled to a source of electrosurgical energy 35 by conductors 36, and a movable, floating electrode 31 selectively positioned in a raised position. The electrodes 32, 34 are brought into contact with tissue T at the targeted area, and the source of electrosurgical energy 35 is activated. Electrosurgical energy flows between electrodes 32, 34 forming a radiating pattern 37 which radiates between electrodes 32, 34. As seen in FIG. 2A, radiating pattern 37 forms not only a relatively direct path directly between electrodes 32, 34, but also radiates away from electrodes 32, 34, which may cause undesired tissue effects peripheral to the targeted tissue area.

Figure 2B:
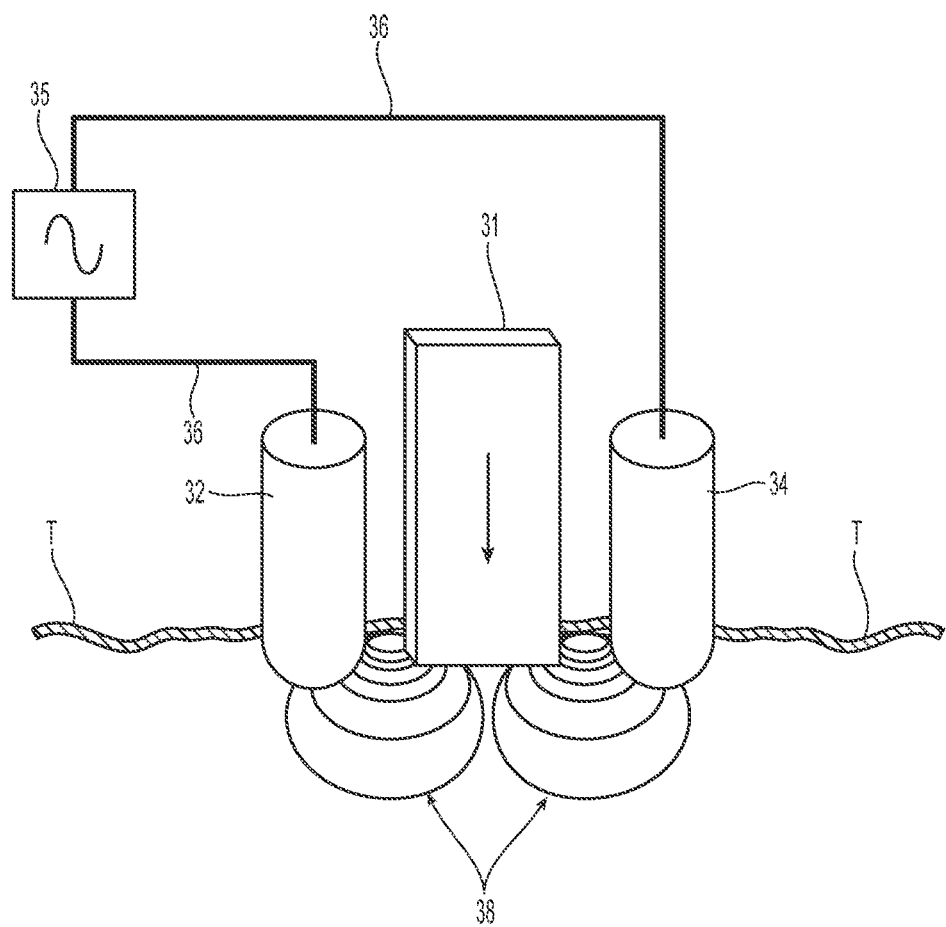
FIG. 2B is a schematic view of bipolar electrodes and a floating electrode in a lowered configuration in accordance with an embodiment of the present disclosure.

Turning to FIG. 2B, where floating electrode 31 is shown in a lowered position in contact with tissue T, a modified radiating pattern 38 is formed when electrosurgical energy is delivered by electrodes 32, 34. As can be seen in FIG. 2B, the modified radiating pattern 38 converges at floating electrode 31 to focus more precisely to the targeted tissue site. In addition, peripheral radiation is decreased. It is believed that the floating electrical potential of floating electrode 31, when positioned between electrodes 32, 34, is determined by the impedance(s) if the tissue T between the electrodes 32, 34 and the electrosurgical current lowing therebetween. Thus the potential of floating electrode 31 falls between the voltages of electrodes 32, 34, which, in turn, creates the modified radiating pattern 38 as illustrated in FIG. 2B.

Advantageously, a surgeon may utilize floating electrode 31 as an additional tool surface with which to dissect tissue T. For example, a surgeon may extend or lower floating electrode 31 and manipulate the entire instrument, bringing electrodes 32, 34 and floating electrode 31 into, and out of, contact with tissue T to work the surgical site. In another example, a surgeon may bring electrodes 32, 34 into substantially continuous contact with tissue T, and manipulate floating electrode 31 up and down using an actuator (e.g., finger trigger or slide as described herein). In yet another example, a surgeon may variously utilize combinations of the above techniques, compound motions, and the like, as required by the instant surgical objective.

Figure 2C:
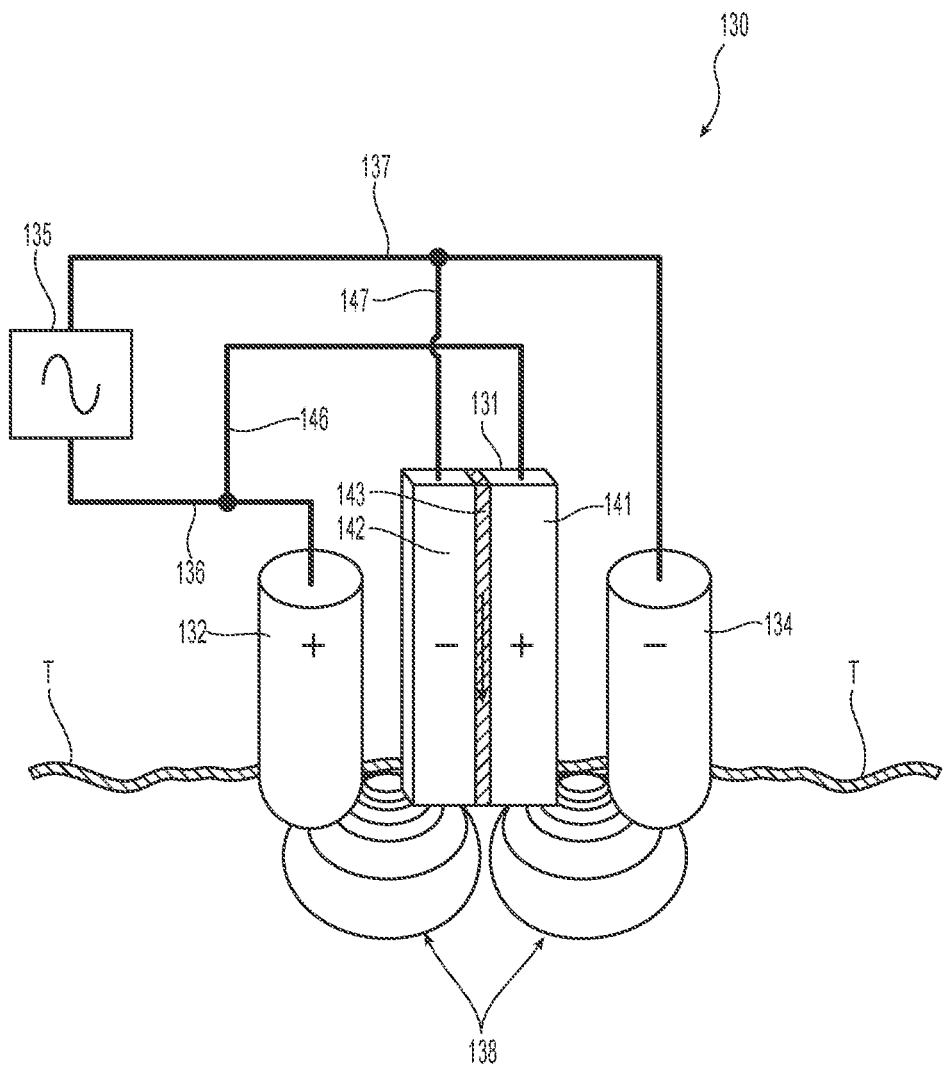
FIG. 2C is a schematic view of bipolar electrodes and a bifurcated electrode having a fixed potential in a lowered configuration in accordance with another embodiment of the present disclosure.

In another aspect of the present disclosure illustrated in FIG. 2C, an electrosurgical instrument 130 includes a movable active electrode 131 that is selectively positionable between fixed active electrodes 132, 134. Active electrode 131 includes two conductive sections 141 and 142 that are electrically isolated by an insulator 143 disposed therebetween. An electrosurgical generator 135 is coupled to electrodes 132, 134 by conductors 136, 137, respectively. Conductive sections 141 and 142 are electrically coupled to fixed active electrodes 132, 134 by conductors 146, 147, respectively. By this arrangement, negative movable active electrode 142 is positionable adjacent to positive fixed active electrode 132, and negative movable active electrode 141 is positionable adjacent to positive fixed active electrode 134. Advantageously, the alternating polarity arrangement of the FIG. 2C electrodes enhances the focus of modified radiating pattern 138, which effectively creates a dual bipolar ablation zone.

Figure 2D:
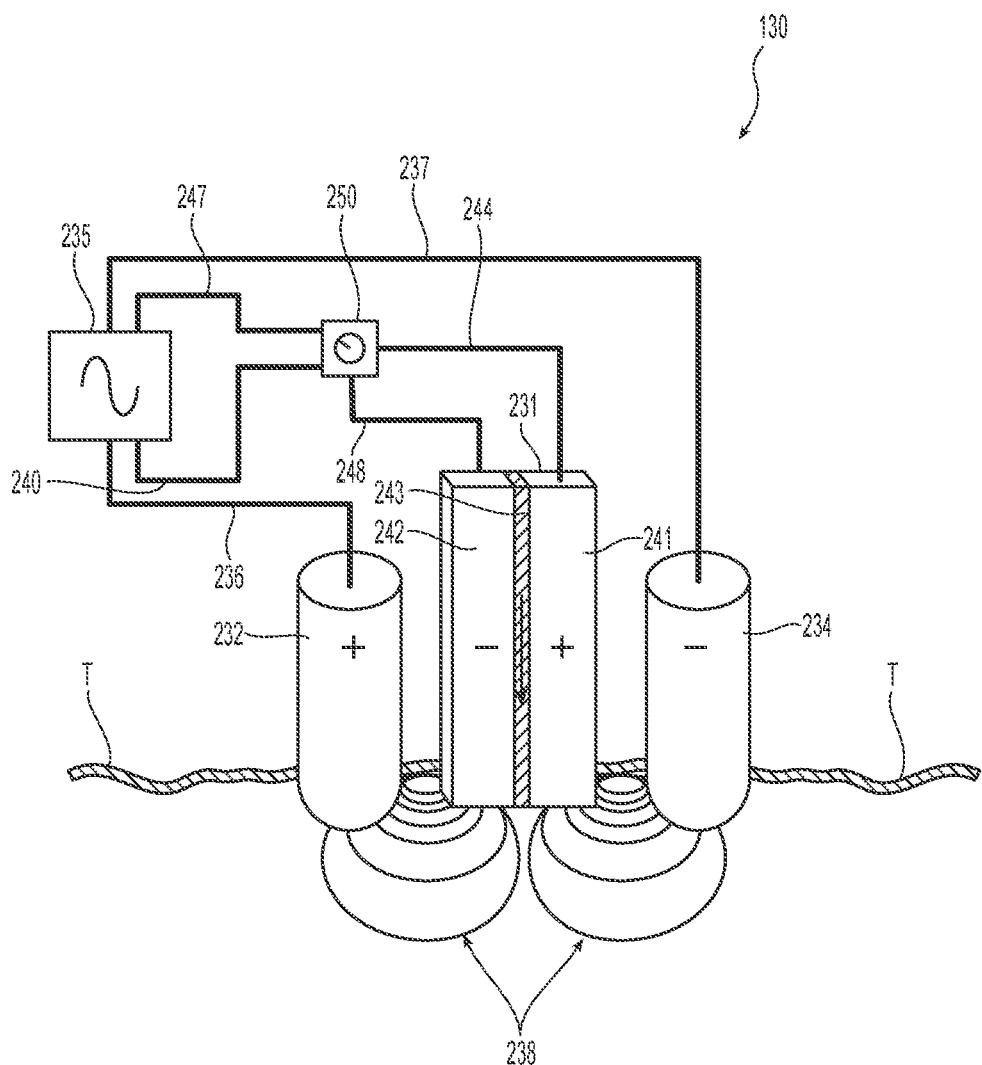
FIG. 2D is a schematic view of bipolar electrodes and a bifurcated electrode having a variable potential in a lowered configuration in accordance with yet another embodiment of the present disclosure.

In yet another aspect of the present disclosure illustrated in FIG. 2D, an electrosurgical instrument 230 includes a movable active electrode 231 that is selectively positionable between fixed active electrodes 232, 234. Active electrode 231 includes two conductive sections 241 and 242 that are electrically isolated by an insulator 243 disposed therebetween. An electrosurgical generator 235 is coupled to electrodes 232, 234 by conductors 236, 237, respectively. Conductive sections 241 and 242 are electrically coupled to a dual-channel intensity control 250 by conductors 244, 248, respectively. Electrosurgical generator 235 is coupled to intensity control 250 by conductors 240 and 247. Intensity control 250 may be continuously variable, and may be user controlled by, e.g., a user interface control such as rotary control (knob) or a linear control (slider or lever). In some embodiments, intensity control 250 may be controlled by a processor and/or in accordance with a tissue parameter, such as, without limitation, tissue temperature, tissue impedance, ablation time, tissue hydration, and/or a rate of change of the same. In some embodiments, intensity control 250 may have an effective range of 0% to 100% of the electrosurgical signal generated by generator 235. In other embodiments, intensity control 250 may have an effective range of −100% to 100% of the electrosurgical signal generated by generator 235. In yet other embodiments, intensity control 250 may have an effective range of 0% to greater than 100% or +/−100% of the electrosurgical signal (e.g., imparting gain to the electrosurgical signal).

Figure 3:
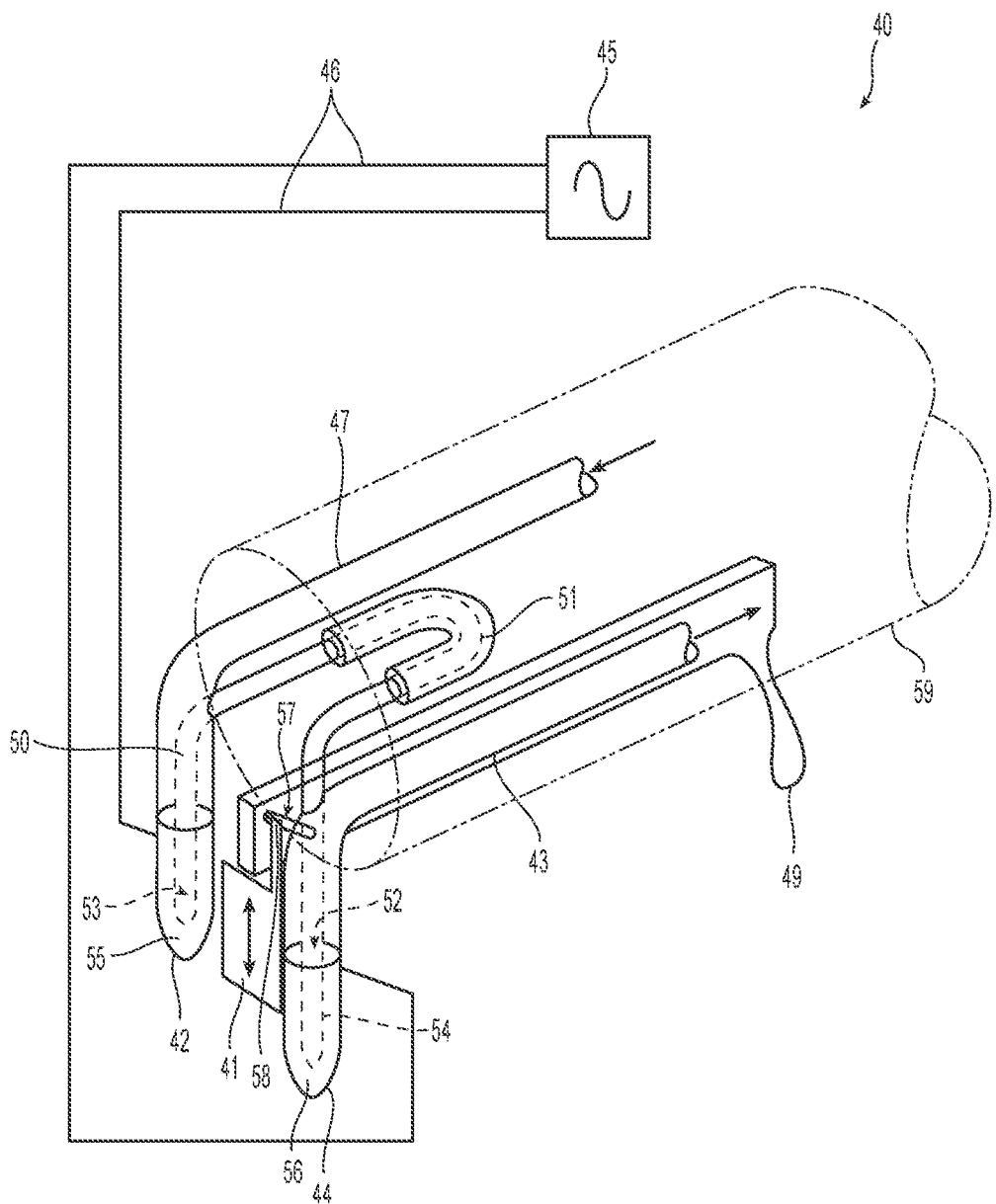
FIG. 3 is a view of an electrosurgical instrument in accordance with an embodiment of the present disclosure having a circulating coolant system.

In another aspect of the present disclosure illustrated in FIG. 3, an electrosurgical instrument 40 includes a coolant supply conduit 47 configured to deliver coolant to first electrode 42, and to second electrode 44. Electrodes 42, 44 are coupled to a source of electrosurgical energy 45 by conductors 46. As shown, electrodes 42 and 44 each include a cooling chamber 55 and 56, respectively, defined therein. Coolant supply conduit 47 is coupled at a distal end thereof to cooling chamber 55 to deliver coolant thereto. An intermediate outflow conduit 50 having a distal opening 53 disposed within cooling chamber 55 is configured to receive coolant exiting from cooling chamber 55. Coolant flows through intermediate outflow conduit 50 to a coupler 51 which is configured to join intermediate outflow conduit 50 and intermediate inflow conduit 52 in fluid communication. In some embodiments, such as that illustrated in FIG. 3, coupler 51 is u-shaped. In some embodiments, coupler 51 is formed from electrically and/or thermally insulative material. Intermediate inflow conduit 52 receives coolant from intermediate outflow conduit 50 via coupler 51, and, in turn, delivers coolant to second electrode 44 via opening 54 disposed within cooling chamber 56. Coolant return conduit 48 is in fluid communication with cooling chamber 56 of electrode 44 to receive coolant exiting from cooling chamber 56 and, in turn, exhausts coolant from instrument 40 to a reservoir, drain, etc.

In other embodiments, the coolant supply may be arranged in a parallel configuration whereby incoming coolant is divided (using, e.g., a "Y" coupling or a manifold) and directed to each electrode, and outgoing coolant from each electrode is joined at a combining junction and exits instrument 40 via coolant return conduit 48.

Instrument 40 includes a floating electrode 41 that is selectively extendible between electrode 42 and electrode 44. A follower 58 is joined to an upper portion of floating electrode 41 that is configured to ride within a cam slot 57 defined in a distal end of a drive member 43. Drive member 43 is configured to move longitudinally, e.g., distally and proximally, and includes a trigger 49 that facilitates manipulation of drive member 43 by a surgeon. As shown in the FIG. 3 embodiment, a distal movement of drive member 43 causes follower 58 to ride downward within cam slot 57, thereby moving floating electrode 41 into an extended, lowered, or deployed, position. Conversely, proximal movement of drive member 43 causes floating electrode 41 to move to a retracted or raised position. Instrument 40 may include ergonomic features, such as, without limitation, a handle (not explicitly shown), a pistol grip (not explicitly shown) or any other suitable features configured to facilitate grasping and use by a surgeon.

Figure 4:
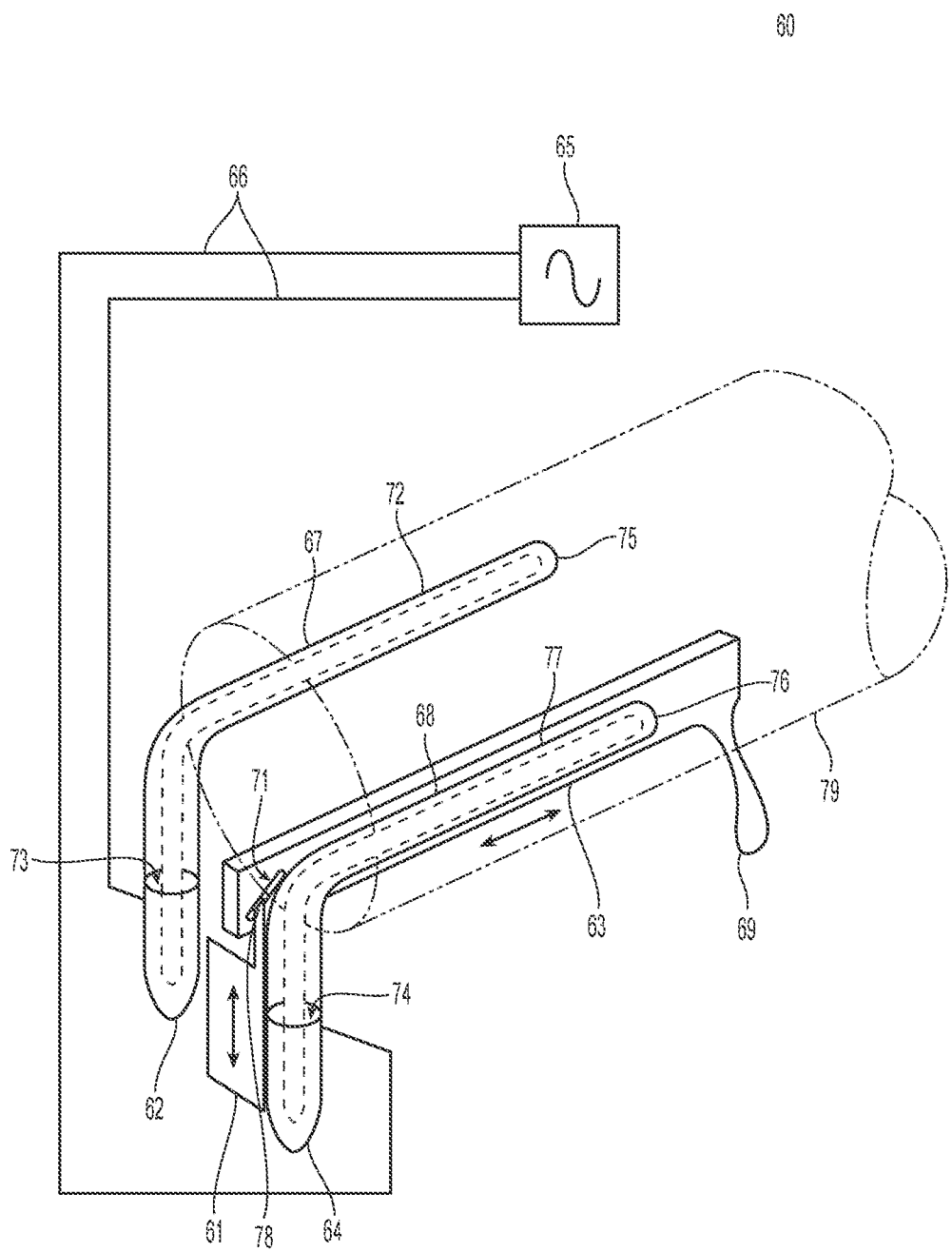
FIG. 4 is a view of an electrosurgical instrument in accordance with an embodiment of the present disclosure having a heat pipe coolant system.

In another aspect of the present disclosure, an embodiment of an electrosurgical instrument 60 is shown in FIG. 4 which includes a first electrode 62 and a second electrode 64 disposed in electrical communication with an electrosurgical generator 65 via conductors 66. A movable floating electrode 61 includes a follower 78 that is configured to engage a cam slot 71 defined in a proximal portion of a drive member 63. Drive member 63 is configured to move distally and proximally, which translates into an up-and-down motion of floating electrode 61 through the cooperation of follower 78 and cam slot 71. Drive member 63 includes a trigger 69 or similar ergonomic feature to facilitate the actuation thereof by a surgeon. Instrument 60 may include ergonomic features, such as, without limitation, a handle 79 or any other suitable features intended to facilitate handling.

Instrument 60 includes a first heat pipe 67 having a hot end 73 that is in thermal communication with electrode 62 and a cool end 75, and a second heat pipe 68 having a hot end 74 that is in thermal communication with electrode 64 and a cool end 76. Heat pipes 67 and 68 may include a heat pipe construction which includes a sealed copper pipe having contained therein a quantity of fluid, such as water or ethanol, and/or a partial vacuum that is near or below the vapor pressure of the fluid. During use, some of the fluid will be in liquid phase and some will be in gas phase. As the hot ends 73, 74 of heat pipes 67, 68 are heated due to thermal effects relating to an electrosurgical procedure, the fluid inside heat pipes 67, 68 vaporizes and increases the vapor pressure therein. The latent heat of evaporation absorbed by the vaporization of the working fluid reduces the temperature at the hot ends 73, 74 of heat pipes 67, 68. The vapors migrate to the respective cool ends 75, 76 of heat pipes 67, 68 where they condense and revert to liquid phase, releasing the absorbed heat. A wick 72, 77 disposed, respectively, within an inner surface of heat pipes 67, 68, absorbs any liquid by capillary action and returns the liquid to the hot ends 73, 74 of heat pipes 67, 68 in an essentially continuous cycle. In some embodiments, cool ends 75, 76 of heat pipes 67, 68 are exposed to the ambient atmosphere, and may include one or more heat sinks (not shown) to facilitate the heat transfer cycle.

Turning to FIGS. 5A-5C, a detailed view of a drive mechanism 80 in accordance with the present disclosure is presented. Drive mechanism 80 is arranged such that a distal motion of an actuation ring 89 results a downward motion of the floating electrode 81. Drive mechanism 80 includes a drive member 83 having a cam slot 87 defined therein at a distal end thereof. As best seen in FIG. 5A, cam slot 87 is angled with respect to the longitudinal axis "A-A" of drive member 83 and has a distal end that is higher than the proximal end. The floating electrode 81 includes a follower 88 joined to an upper portion of the floating electrode 81 by an extension 86. In some embodiments, floating electrode 81, extension 86, and follower 88 may be integrally formed from sheet metal using a punching and/or stamping process. In some embodiments, floating electrode 81, extension 86, and follower 88 may be formed from stainless steel. Follower 88 is disposed at an angle with respect to floating electrode 81 which substantially corresponds to the angle of cam slot 87. In the FIGS. 5A-5C embodiments, where forward (distal) motion of the drive member 83 causes downward deployment of floating electrode 81, an actuation ring 89 may be provided to enable a surgeon to readily manipulate drive member 83 in either a distal or proximal direction.

In another embodiment depicted in FIGS. 6A and 6B, a drive mechanism 90 in accordance with the present disclosure is arranged such that proximal motion of an actuation trigger 99 results a downward motion of the floating electrode 91. Drive mechanism 90 includes a drive member 93 having a cam slot 97 defined therein at a distal end thereof. Here, cam slot 97 is angled with respect to the longitudinal axis "B-B" of drive member 93 such that the distal end of cam slot 97 is lower than the proximal end of cam slot 97. Floating electrode 91 includes a follower 98 joined to an upper portion of the floating electrode 91 by an extension 96. Follower 98 is disposed at an angle which substantially corresponds to the angle of cam slot 97. Rearward (proximal) motion of drive member 93 causes downward deployment of floating electrode 91. In this embodiment, trigger 99 is provided to enable the surgeon to intuitively manipulate drive member 93 in proximal direction to deploy floating electrode 91. A return spring 95 is provided which biases drive member 93 in a distal direction, thus when a surgeon releases pressure on trigger 99, drive member 93 is driven distally and floating electrode 91 is moved upwardly through the cooperation of follower 98 and cam slot 97.

Turning now to FIGS. 7A-7G, yet another embodiment of a drive mechanism 100 for a floating electrode 101 is presented. Floating electrode 101 is formed from a strip of flexible material, such as spring steel, Nitinol (or other shape memory metal), and/or a high-temperature-resistant composite material. A proximal end of floating electrode 101 is joined to a drive member 103 by a pin 102. Drive member 103 includes a thumb actuator 109 which is configured to be manipulated a surgeon to effectively lower and raise floating electrode 101. A distal portion of floating electrode 101 passes through an L-shaped electrode guide 108 having a channel 107 defined therein. Channel 107 includes an entrance 105 into which floating electrode 101 is introduced and an exit 106 through which floating electrode 101 extends toward tissue.

Electrode guide 108 includes a 90° transition elbow having a radius a which enables the distal portion of floating electrode 101, as it is advanced distally by drive member, to bend downwardly and thus extend into a lowered position between the bipolar electrodes (not explicitly shown). As can be seen in FIG. 7F, a cross section of channel 107 adjacent to radius a is substantially straight, enabling the flexible floating electrode 101 to remain flat and thus allowing floating electrode 101 to flex easily as it is advanced through radius a during deployment of floating electrode 101 into position between electrodes. As channel 107 approaches exit 106, the cross section of channel 107 become slightly curved as shown in FIGS. 7E and 7G. As flexible floating electrode 101 extends from exit 106, this curve is imparted to floating electrode 101 (FIG. 7E), which, in turn, provides rigidity and stiffness to the extended portion 110 of floating electrode 101.

In some embodiments, the inner surface of channel 107 and/or the outer surface of flexible floating electrode 101 may include a lubricious coating, such as, without limitation, polytetrafluoroethylene (PTFE).

The various embodiments disclosed herein may also be configured to work with robotic surgical systems and what is commonly referred to as "Telesurgery". Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely activatable active electrodes, a remotely positionable floating electrode, remotely steerable systems, remotely articulating surgical systems, wireless surgical systems, modular, or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions, such as contacting the active electrode to targeted tissue, extending and/or retracting the floating electrode, controlling the delivery of electrosurgical energy, and so forth.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument, comprising:
   a shaft;
   a first active electrode and a second active electrode disposed in spaced relation on a distal portion of the shaft, a tip of the first active electrode and a tip of the second active electrode disposed within a common plane; and
   a floating electrode selectively positionable between an extended position where the floating electrode is disposed within an area between the first active electrode and the second active electrode, and a retracted position where the floating electrode is removed from the area between the first active electrode and the second active electrode, wherein the floating electrode is parallel to the plane when the floating electrode is in both the extended position and in the retracted position, wherein when the floating electrode is in the extended position, at least a majority of the floating electrode is radially outside of a circumferential edge of the shaft.

2. The electrosurgical instrument according to claim 1, wherein the tip of the first active electrode and the tip of the second active electrode extend radially outside of the circumferential edge of the shaft.

3. The electrosurgical instrument according to claim 1, wherein the first active electrode is fixed from movement with respect to the second active electrode and with respect to the shaft.

4. The electrosurgical instrument according to claim 1, wherein when the floating electrode is in the extended position, the first active electrode is located on a first lateral side of the floating electrode and the second active electrode is located on a second lateral side of the floating electrode, the first lateral side of the floating electrode being opposite from the second lateral side of the floating electrode.

5. The electrosurgical instrument according to claim 1, wherein when the floating electrode is in the extended position, a tissue-contacting surface of the first active electrode, a tissue-contacting surface of the second active electrode, and a tissue-contacting surface of the floating electrode lie substantially in the same plane.

6. The electrosurgical instrument according to claim 1, further comprising:
a coolant supply conduit configured to deliver coolant to the first active electrode and the second active electrode; and
a coolant return conduit configured to remove coolant from the first active electrode and the second active electrode.

7. The electrosurgical instrument according to claim 1, further comprising a drive mechanism, including:
a drive member movable along a longitudinal axis defined by the shaft between a first position and a second position;
a cam slot defined in a distal end of the drive member; and
a follower fixed to the floating electrode and configured to operably engage the cam slot, wherein when the drive member is in a first position, the floating electrode is in the extended position and wherein when the drive member is in a second position the floating electrode is in the retracted position.

8. The electrosurgical instrument according to claim 1, wherein a distal-most end of the floating electrode is between distal portions of the first active electrode and the second active electrode when the floating electrode is in a fully retracted position.

9. The electrosurgical system according to claim 1, wherein the floating electrode is movable relative to the first active electrode in a direction that is perpendicular with respect to a longitudinal axis defined by the shaft.

10. The electrosurgical instrument according to claim 1, wherein the floating electrode is parallel to the tip of the first active electrode and the tip of the second active electrode while the floating electrode moves between the extended position and the retracted position.

11. The electrosurgical instrument according to claim 1, wherein the floating electrode is disposed in non-pivotable relation relative to the shaft.

12. An electrosurgical instrument, comprising:
a shaft defining a longitudinal axis;
a first active electrode and a second active electrode disposed in spaced relation on a distal portion of the shaft; and
a floating electrode selectively positionable between an extended position where the floating electrode is disposed within an area between the first active electrode and the second active electrode, and a retracted position where the floating electrode is displaced from the area between the first active electrode and the second active electrode, wherein the floating electrode is only movable relative to the first active electrode in a direction that is perpendicular to the longitudinal axis.

13. The electrosurgical instrument according to claim 12, wherein a tip of the first active electrode and a tip of the second active electrode extend radially outside of a circumferential edge of the shaft.

14. The electrosurgical instrument according to claim 13, wherein when the floating electrode is in the extended position, at least a majority of the floating electrode is radially outside of the circumferential edge of the shaft.

15. The electrosurgical instrument according to claim 12, wherein the first active electrode is immovable with respect to the second active electrode and with respect to the shaft.

16. The electrosurgical system according to claim 12, wherein when the floating electrode is in the extended position, a tissue-contacting surface of the first active electrode, a tissue-contacting surface of the second active electrode, and a tissue-contacting surface of the floating electrode lie substantially in the same plane.

17. A method for electrosurgically treating tissue, comprising:
applying a first active electrode and a second active electrode of an electrosurgical surgical instrument to tissue;
delivering electrosurgical energy to tissue via the first active electrode and the second active electrode;
moving a floating electrode of the electrosurgical instrument from an extended position to a retracted position in a direction parallel to a tip of the first active electrode and a tip of the second active electrode, and within a plane that includes the tip of the first active electrode and the tip of the second active electrode, while moving the floating electrode in a direction that is perpendicular to a longitudinal axis defined by a shaft of the electrosurgical instrument; and
applying the floating electrode to tissue.

18. The method for electrosurgically treating tissue according to claim 17, wherein when the floating electrode is in the extended position, at least a majority of the floating electrode is radially outside of a circumferential edge of the shaft.

19. The method for electrosurgically treating tissue according to claim 17, further comprising dissecting tissue using the floating electrode.

* * * * *